(12) United States Patent
Michel

(10) Patent No.: US 9,072,295 B2
(45) Date of Patent: Jul. 7, 2015

(54) HERBICIDAL COMPOSITIONS

(75) Inventor: Albrecht Michel, Basel (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/119,515

(22) PCT Filed: May 31, 2012

(86) PCT No.: PCT/EP2012/060234
§ 371 (c)(1),
(2), (4) Date: Nov. 22, 2013

(87) PCT Pub. No.: WO2012/164012
PCT Pub. Date: Dec. 6, 2012

(65) Prior Publication Data
US 2014/0087947 A1    Mar. 27, 2014

(30) Foreign Application Priority Data

Jun. 1, 2011   (EP) ...................... 1109239

(51) Int. Cl.

| | |
|---|---|
| *A01N 25/32* | (2006.01) |
| *A01N 41/06* | (2006.01) |
| *A01N 43/84* | (2006.01) |
| *A01N 43/653* | (2006.01) |
| *A01N 37/48* | (2006.01) |
| *A01N 33/22* | (2006.01) |
| *A01N 37/18* | (2006.01) |

(52) U.S. Cl.
CPC ............... *A01N 25/32* (2013.01); *A01N 41/06* (2013.01); *A01N 43/84* (2013.01); *A01N 43/653* (2013.01); *A01N 37/48* (2013.01); *A01N 33/22* (2013.01); *A01N 37/18* (2013.01)

(58) Field of Classification Search
None
See application file for complete search history.

(56) References Cited

U.S. PATENT DOCUMENTS 8,648,011 B2 * 2/2014 Michel et al. ............... 504/100

FOREIGN PATENT DOCUMENTS

| EP | 0365484 | | 4/1990 |
|---|---|---|---|
| EP | 1388285 | | 2/2004 |
| EP | 1952688 | | 8/2008 |
| EP | 2145537 | * | 1/2010 |
| WO | 99/66795 | | 12/1999 |
| WO | 01/08487 | | 2/2001 |
| WO | WO-0108487 | * | 2/2001 |
| WO | 03/047343 | | 6/2003 |

OTHER PUBLICATIONS

International Search Report, International Application No. PCT/EP2012/060234, completion date: Feb. 8, 2012.

* cited by examiner

Primary Examiner — Alton Pryor
(74) Attorney, Agent, or Firm — James Cueva

(57) ABSTRACT

The present invention provides, inter alia, a herbicidal composition comprising: (i) a protoporphyrinogen oxidase inhibiting herbicide selected from the group consisting flumioxazin, sulfentrazone, butafenacil and a diphenyl ether selected from the group consisting of acifluorfen (including acifluorfen-sodium), fomesafen (including fomesafen-sodium), lactofen and oxyfluorfen; or an agronomically acceptable salt of said herbicide; and (ii) a safener of Formula (II) or an agronomically acceptable salt of said compound, wherein: —$R^a$ is selected from the group consisting of halogen, nitro, $C_1$-$C_4$ alkyl, $C_1$-$C_4$ haloalkyl, $C_1$-$C_4$ haloalkoxy, $C_3$-$C_6$ cycloalkyl, phenyl, $C_1$-$C_4$ alkoxy, cyano, $C_1$-$C_4$ alkylthio, $C_1$-$C_4$ alkylsulfinyl, $C_1$-$C_4$ alkylsulfonyl, $C_1$-$C_4$ alkoxycarbonyl and $C_1$-$C_4$ alkylcarbonyl; and $R^b$ and $R^c$ are independently selected from the group consisting of hydrogen, $C_1$-$C_6$ alkyl, $C_3$-$C_6$ cycloalkyl, $C_3$-$C_6$ alkenyl and $C_3$-$C_6$ alkynyl.

(II)

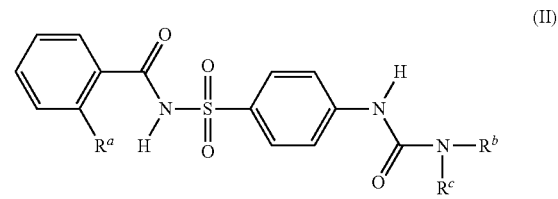

10 Claims, No Drawings

HERBICIDAL COMPOSITIONS

This application is a 371 of International Application No. PCT/EP2012/060234 filed May 31, 2012, which claims priority to EP 1109239.2, filed Jun. 1, 2011, the contents of which are incorporated herein by reference.

The present invention relates to improved herbicidally active compositions comprising certain protoporphyrinogen oxidase (PPGO) inhibiting herbicides and certain defined herbicide safeners. The present invention further relates to the use of the improved herbicidal compositions for controlling weeds, in particular in crop plants, which are safer to crop plants (i.e exhibit less phytotoxicity).

Protoporphyrinogen oxidase inhibiting herbicides are known in the art. However, these herbicides can exhibit unacceptable levels of phytotoxicity in crop plants. There exists a need therefore to provide improved herbicidal compositions which exhibit reduced crop phytotoxicity—and it has now been discovered that certain N-acylsulfamoylphenylurea safeners—hitherto not taught in combination with these herbicides—are surprisingly effective in safening these compounds in crop plants.

Thus, according to the present invention there is provided a herbicidal composition comprising:

(i) a protoporphyrinogen oxidase inhibiting herbicide selected from the group consisting of flumioxazin, sulfentrazone, butafenacil and a diphenyl ether selected from the group consisting of acifluorfen (including aciflurofen-sodium), fomesafen (including fomesafen-sodium), lactofen and oxyfluorfen; or an agronomically acceptable salt of said herbicide; and (ii) a safener of Formula (II);

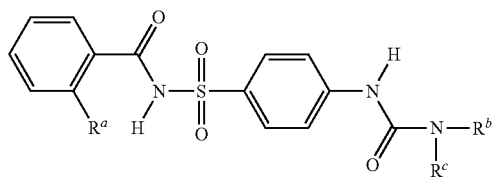

or an agronomically acceptable salt of said compound, wherein:

$R^a$ is selected from the group consisting of halogen, nitro, $C_1$-$C_4$ alkyl, $C_1$-$C_4$ haloalkyl, $C_1$-$C_4$ haloalkoxy, $C_3$-$C_6$ cycloalkyl, phenyl, $C_1$-$C_4$ alkoxy, cyano, $C_1$-$C_4$ alkylthio, $C_1$-$C_4$ alkylsulfinyl, $C_1$-$C_4$ alkylsulfonyl, $C_1$-$C_4$ alkoxycarbonyl and $C_1$-$C_4$ alkylcarbonyl; and $R^b$ and $R^c$ are independently selected from the group consisting of hydrogen, $C_1$-$C_6$ alkyl, $C_3$-$C_6$ cycloalkyl, $C_3$-$C_6$ alkenyl and $C_3$-$C_6$ alkynyl.

Halogen encompasses fluorine, chlorine, bromine or iodine. The same correspondingly applies to halogen in the context of other definitions, such as haloalkyl. Haloalkyl groups are thus, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl and heptafluoro-n-propyl.

Alkoxy is, for example, methoxy, ethoxy, propoxy, isopropoxy, n-butoxy, isobutoxy, sec-butoxy or tert-butoxy, preferably methoxy and ethoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Cycloalkyl groups preferably have from 3 to 6 ring carbon atoms and may be substituted by one or more methyl groups; they are preferably unsubstituted, for example cyclopropyl, cyclobutyl, cyclopentyl or cyclohexyl.

In a preferred embodiment of the present invention the protoporphyrinogen oxidase inhibiting herbicide is selected from the group consisting of flumioxazin, sulfentrazone and fomesafen (including fomesafen-sodium). In an especially preferred embodiment the protoporphyrinogen oxidase inhibiting herbicide is fomesafen (or fomesafen-sodium).

Safeners of Formula (II) are known from EP-A-365484. In a preferred embodiment the safener of is of Formula (II) in which $R^a$ is $C_1$-$C_4$ alkoxy, preferably methoxy; $R^b$ is $C_1$-$C_6$ alkyl, preferably methyl and $R^c$ is hydrogen or methyl. In a particularly preferred embodiment the safener is 1-[4-(N-2-methoxybenzoylsulfamoyl) phenyl]-3-methylurea.

The herbicide:safener ratio in the herbicidal composition may vary depending on the exact nature of the intended application. Typically the ratio will be from 100:1 to 1:100 on a weight for weight basis, preferably from 100:1 to 1:50, more preferably from 25:1 to 1:25.

The herbicidal compositions of the present invention will typically be formulated using in the art recognised formulation adjuvants, such as carriers, solvents and surface-active agents (SFAs). Thus, the present invention further provides a herbicidal composition further comprising an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), suspo-emulsions (SE), aerosols, capsule suspensions (CS) and seed treatment formulations.

The herbicidal composition of the present invention may further comprise at least one additional pesticide, for example a nematicide, an insecticide, a fungicide and/or a herbicide. Examples of suitable pesticides are listed in "The Pesticide Manual", Fourteenth Edition (2006), Editor, C. D. S. Tomlin. Preferably, the additional pesticide is one or more herbicides selected from the group consisting of glyphosate, glufosinate, cafentrazone-ethyl, fluthiacet, flumiclorac, metolachlor, S-metolachlor, acetochlor, alachlor, pyroxasulfone, flufenacet, dimethenamid, dimethenamid-P, bromoxynil, bentazon, metribuzin, atrazine, terbuthylazine, diuron, fluazifop, clethodim, fenoxaprop, haloxyfop, bensulfuron, nicosulfuron, rimsulfuron, primisulfuron, thifensulfuron, foramsulfuron, chlorsulfuron, halosulfuron, imaziquin, imazapic, imazapic, imazapyr imazethapyr, imazamox, iodosulfuron, metsulfuron, mesosulfuron sulfosulfuron trifloxysulfuron tribenuron methyl, saflufenacil, thiazopyr, tebuthiuron, cloransulam-methyl, flucarbazone, flumetsulam amicarbazone, thiencarbazone, chlorimuron-ethyl, dicamba, 2,4-D, 2,4-DB, fluroxypyr, diflufenzopry, tirclopry, picloram, quinclorac, clopyralid and aminopyralid; or agrochemically acceptable salts thereof.

In a particular embodiment the herbicidal composition does not comprise a herbicidal compound of Formula (I):

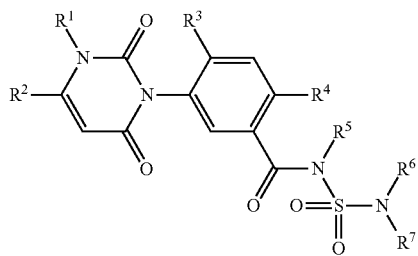

or an agronomically acceptable salt of said compound, wherein:
$R^1$ is methyl or $NH_2$;
$R^2$ is $C_1$-$C_2$ haloalkyl;
$R^3$ is hydrogen of halogen;
$R^4$ is halogen or cyano;
$R^5$ is selected from the group consisting of hydrogen, cyano, $C_1$-$C_6$ alkyl, $C_1$-$C_6$ alkoxy, $C_1$-$C_4$ alkoxy-$C_1$-$C_4$alkyl, $C_3$-$C_7$ cycloalkyl, $C_3$-$C_6$alkenyl, $C_3$-$C_6$ alkynyl and benzyl which is optionally substituted by halogen and/or $C_1$-$C_6$ alkyl; and
$R^6$ and $R^7$ are independently selected from the group consisting of hydrogen, $C_1$-$C_6$ alkyl, $C_1$-$C_6$ alkoxy, $C_3$-$C_6$ alkenyl, $C_3$-$C_6$ alkynyl, $C_3$-$C_7$ cycloalkyl, $C_3$-$C_7$ cycloalkenyl, phenyl and benzyl, wherein each of the eight above-mentioned substituents is optionally substituted by one to six halogen atoms and/or by one, two or three groups selected from: OH, $NH_2$, CN, $CONH_2$, $C_1$-$C_4$ alkoxy, $C_1$-$C_4$ haloalkoxy, $C_1$-$C_4$ alkylthio, $C_1$-$C_4$ haloalkylthio, $C_1$-$C_4$alkylsulfonyl, $C_1$-$C_4$ haloalkylsulfonyl, $C_1$-$C_4$ alkylamino, di($C_1$-$C_4$-alkyl)amino, formyl, $C_1$-$C_6$ alkylcarbonyl, $C_1$-$C_4$ alkoxycarbonyl, $C_1$-$C_4$ alkylaminocarbonyl, di($C_1$-$C_4$ alkyl)aminocarbonyl, $C_3$-$C_7$ cycloalkyl, phenyl and benzyl.

The herbicidal composition applied to the locus may also further comprise an additional herbicide safener.

The present invention still further provides a method of selectively controlling weeds at a locus comprising crop plants and weeds, wherein the method comprises application to the locus of a weed controlling amount of:

(i) a protoporphyrinogen oxidase inhibiting herbicide selected from the group consisting flumioxazin, sulfentrazone, butafenacil and a diphenyl ether selected from the group consisting of acifluorfen (including acifluorofen-sodium), fomesafen (including fomesafen-sodium), lactofen and oxyfluorfen; or an agronomically acceptable salt of said herbicide; and (ii) a safener of Formula (II);

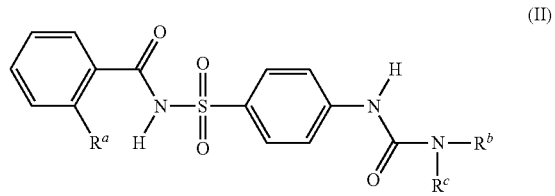

or an agronomically acceptable salt of said compound, wherein:
$R^a$ is selected from the group consisting of halogen, nitro, $C_1$-$C_4$ alkyl, $C_1$-$C_4$ haloalkyl, $C_1$-$C_4$ haloalkoxy, $C_3$-$C_6$ cycloalkyl, phenyl, $C_1$-$C_4$ alkoxy, cyano, $C_1$-$C_4$ alkylthio, $C_1$-$C_4$ alkylsulfinyl, $C_1$-$C_4$ alkylsulfonyl, $C_1$-$C_4$ alkoxycarbonyl and $C_1$-$C_4$ alkylcarbonyl; and
$R^b$ and $R^c$ are independently selected from the group consisting of hydrogen, $C_1$-$C_6$ alkyl, $C_3$-$C_6$ cycloalkyl, $C_3$-$C_6$ alkenyl and $C_3$-$C_6$ alkynyl.

'Controlling' means killing, reducing or retarding growth or preventing or reducing germination. Generally the plants to be controlled are unwanted plants (weeds). 'Locus' means the area in which the plants are growing or will grow.

Components (i) and (ii) can be independently applied to the locus pre-planting, pre-emergence and/or post emergence. By "pre-planting" it is meant that the herbicidal composition is applied before the crop is planted at the locus, by "pre-emergence" it is meant that the herbicidal composition is applied before the germinating crop plant seed emerges above the locus surface and by "post-emergence" it is meant that the herbicide composition is applied once the crop plant is visible above the locus surface. Component (ii) may also be applied to the seed of the crop plant as a seed treatment prior to sowing. Such seed treatment has added utility in that it helps protect the seed from any residual herbicide of Formula (I) which may be present at the locus, for example from previous applications of herbicide to the locus. Thus, in preferred embodiments of the described method seeds treated with component (ii) are sown at the locus, followed by the application of component (i) optionally combined with an additional component (ii) application. Alternatively, components (i) and (ii) will be applied to the locus in a single combined pre or post-emergence application.

The rates of application of components (i) and (ii) will vary depending on the particular application (e.g method of application (pre- or post-emergence; seed dressing; application to the seed furrow; no tillage application etc.), the crop plant, the weed(s) to be controlled, the prevailing climatic conditions, and other factors governed by the method of application, the time of application and the target crop). Typically, the rate of application of herbicide (i) will be from 10 to 4000 g ha, suitably from 10 to 2500 g/ha, more suitably from 50 to 500 g/ha. The rate of application of the safener component (ii) is suitably from 5 to 500 g/ha, more suitably from 10 to 100 g/ha. If the safener is to be applied as a seed treatment, then it can suitably be applied from 0.1 to 10 g safener per kg seed—typically 1 g safener per kg seed.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sorghum, switch grass and sugar cane. Maize, along with wheat, are however particularly preferred. Crop plants can also include turf and trees, such as fruit trees, palm trees, coconut trees or other nuts. Also included are vines such as grapes, fruit bushes, fruit plants and vegetables. It should be understood that the crop plants also include those which have been genetically engineered so as to be tolerant to one or more additional herbicides, insects, fungal, bacterial and/or viral infections. Examples are crop plants which comprise glyphosate tolerant 5-enol-pyruvylshikimate-3-phosphate synthase (EPSPS) (for example as disclosed in U.S. Pat. No. 5,804,425, U.S. Pat. No. 6,566,587), glyphosate N-acetyl transferase (GAT) (for example as disclosed in WO02/036782), herbicide tolerant 4-hydroxy-pyruvyldioxgenase (HPPD) (for example as disclosed in WO02/46387), phosphinothricin acetyl transferase (PAT) (for example as disclosed in U.S. Pat. No. 5,273,894), cytochrome P450 (for example as disclosed in WO 07/103567), glutathione S-transferase (GST) (for example as disclosed in WO01/21770), herbicide tolerant acetyl-COA-carboxylase (ACCase), herbicide tolerant acetolactate synthase (ALS) (for example as disclosed in U.S. Pat. No. 5,013,659), herbicide tolerant protoporphyrinogen oxidase (PPGO) (for example as disclosed in WO95/34659), bromoxynil nitrilase (for example, as disclosed in WO89/00193), herbicide tolerant phytoene desaturase (for example as disclosed in EP0393690), aryloxyalkanoate dioxygenase (for example as disclosed in WO2005/107437 and WO2007/053482) and dicamba degrading enzymes (for example as disclosed in WO98/45424); including known mutagenised or otherwise modified variants of these polypeptides.

The compositions can be used to control unwanted plants (collectively, 'weeds'). The weeds to be controlled may be both monocotyledonous species, for example *Agrostis, Alopecurus, Avena, Bromus, Cyperus, Digitaria, Echinochloa, Lolium, Monochoria, Rottboellia, Sagittaria, Scirpus, Setaria, Sida* and *Sorghum*, and dicotyledonous species, for example *Abutilon, Amaranthus, Chenopodium, Chrysanthemum, Conyza, Galium, Ipomoea, Nasturtium, Sinapis, Solanum, Stellaria, Veronica, Viola* and *Xanthium*. Weeds can also include plants which may be considered crop plants but which are growing outside a crop area (escapes), or which grow from seed left over from a previous planting of a different crop (volunteers). Such volunteers or escapes may be tolerant to certain other herbicides.

BIOLOGICAL EXAMPLES

Experiment 1

Winter wheat seed is treated with safener A (1-[4-(N-2-methoxybenzoylsulfamoyl)phenyl]-3-methylurea) at 100 g safener/100 kg of seed. Control seed is also included which contains no safener seed treatment. The wheat seed is then planted in a field as a randomized block design including four replications. Fomesafen (as Reflex™) is applied pre-emergence (after planting) using a backpack sprayer. Herbicidal damage to the emerged wheat plants is assessed and the results obtained are summarized in Table 1 below. These results indicate that the safener applied provides highly effective safening of the diphenyl ether herbicide fomesafen, even at the highest application rate tested of 560 g/ha.

TABLE 1

| Fomesafen Rate g/ha | % Phytotoxicity Control | Safener A Treated Seed |
|---|---|---|
| 0 g/ha | 0 | 0 |
| 70 g/ha | 0 | 0 |
| 140 g/ha | 1 | 0 |
| 280 g/ha | 18 | 0 |
| 560 g/ha | 71 | 0 |

Experiment 2

A greenhouse study is performed to evaluate the safener response of various maize varieties to various PPGO inhibiting herbicides. Seeds from various maize varieties (LEXXOR, PACTOL, CLAXXON, GARLAND and SUNDANCE) are treated with either safener A (1-[4-(N-2-methoxybenzoylsulfamoyl)phenyl]-3-methylurea) or benoxacor at a rate of 1 g safener/kg of seed. Control seed is also included in the test which contains no safener seed treatment. Herbicide treatments are applied pre-emergence, at the indicated application rates, using a laboratory tracksprayer with a TeeJet 11002VS nozzle. The sprayer is set to deliver an output of 200 L/ha by applying an air pressure of 2 bar. The treated and control seeds are then planted in the treated sandy loam soil contained in 10 cm deep plastic trays and watered from the top of the trays as needed. Herbicidal damage to the emerged maize plants is then assessed 8 days after application (DAA) of the herbicide and the results obtained are summarized in Table 2 below (averaged values across the various maize lines used are provided). These results indicate that safener A provides highly effective safening of the various PPGO inhibiting herbicides tested—with particularly good safening observed against sulfentrazone.

| Product | Rate gai/ha | untreated | Benoxacor | Safener A |
|---|---|---|---|---|
| Fomesafen - Reflex (SL240) | 31.25 | 0 | 1 | 0 |
| | 62.5 | 7 | 17 | 2 |
| | 125 | 36 | 34 | 19 |
| | 250 | 74 | 73 | 51 |
| | 500 | 86 | 88 | 69 |
| Flumioxazin - Valor (WG51) | 15.625 | 7 | 7 | 4 |
| | 31.25 | 25 | 12 | 7 |
| | 62.5 | 31 | 32 | 14 |
| | 125 | 48 | 43 | 34 |
| | 250 | 70 | 53 | 51 |
| Sulfentrazone - Authority (SC500) | 31.25 | 1 | 0 | 1 |
| | 62.5 | 5 | 0 | 0 |
| | 125 | 10 | 9 | 2 |
| | 250 | 51 | 55 | 7 |
| | 500 | 73 | 89 | 9 |
| Butafenacil (WG71.4) | 125 | 21 | 27 | 10 |
| | 250 | 36 | 37 | 11 |
| | 500 | 65 | 63 | 32 |
| | 1000 | 92 | 88 | 53 |
| | 2000 | 98 | 97 | 76 |
| Acifluorfen - Blazer (SL188.6) | 312.5 | 3 | 9 | 7 |
| | 625 | 24 | 22 | 24 |
| | 1250 | 56 | 60 | 47 |
| | 2500 | 81 | 75 | 71 |
| | 5000 | 92 | 92 | 81 |
| Lactofen - Cobra (EC240) | 312.5 | 15 | 18 | 13 |
| | 625 | 27 | 25 | 23 |
| | 1250 | 44 | 51 | 40 |
| | 2500 | 54 | 63 | 52 |
| | 5000 | 66 | 61 | 53 |
| Oxyfluorfen - Goal | 125 | 44 | 47 | 26 |

-continued

| Product | Rate gai/ha | untreated | Benoxacor | Safener A |
|---------|-------------|-----------|-----------|-----------|
| (EC240) | 250 | 67 | 66 | 50 |
| | 500 | 85 | 81 | 72 |
| | 1000 | 95 | 90 | 85 |
| | 2000 | 98 | 95 | 91 |

The invention claimed is:

1. A herbicidal composition comprising:
(i) a protoporphyrinogen oxidase inhibiting herbicide selected from the group consisting flumioxazin, sulfentrazone, butafenacil and a diphenyl ether selected from the group consisting of acifluorfen, fomesafen, lactofen and oxyfluorfen; or an agronomically acceptable salt of said herbicide; and
(ii) a safener of Formula (II);

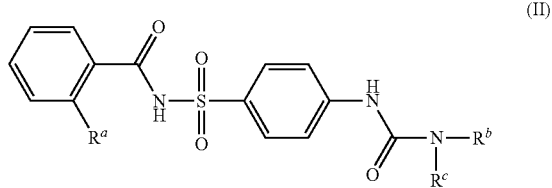

(II)

or an agronomically acceptable salt of said compound, wherein:—
$R^a$ is selected from the group consisting of halogen, nitro, $C_1$-$C_4$ alkyl, $C_1$-$C_4$ haloalkyl, $C_1$-$C_4$ haloalkoxy, $C_3$-$C_6$ cycloalkyl, phenyl, $C_1$-$C_4$ alkoxy, cyano, $C_1$-$C_4$ alkylthio, $C_1$-$C_4$ alkylsulfinyl, $C_1$-$C_4$ alkylsulfonyl, $C_1$-$C_4$ alkoxycarbonyl and $C_1$-$C_4$ alkylcarbonyl; and
$R^b$ and $R^c$ are independently selected from the group consisting of hydrogen, $C_1$-$C_6$ alkyl, $C_3$-$C_6$ cycloalkyl, $C_3$-$C_6$ alkenyl and $C_3$-$C_6$ alkynyl.

2. A herbicidal composition accordingly to claim 1, wherein the protoporphyrinogen oxidase inhibiting herbicide is selected from the group consisting flumioxazin, sulfentrazone, and fomesafen; or an agronomically acceptable salt thereof.

3. A herbicidal composition according to claim 1, wherein the herbicide is fomesafen or an agronomically acceptable salt thereof.

4. A herbicidal composition according to claim 1, wherein the safener is a compound of Formula (II) wherein:
$R^a$ is $C_1$-$C_4$ alkoxy;
$R^b$ is $C_1$-$C_6$ alkyl; and
$R^c$ is hydrogen.

5. A herbicidal composition according to claim 1, further comprising at least one additional pesticide.

6. A method of selectively controlling weeds at a locus comprising crop plants and weeds, wherein the method comprises application to the locus of a weed controlling amount of a herbicidal composition according to claim 1.

7. A method according to claim 6, wherein the crop plants are selected from the group consisting of barley, oats, sorghum, wheat, cotton, maize, rice, switch grass and sugar cane.

8. A method according to claim 7, wherein the crop plant is wheat or maize.

9. A method according to claim 6, wherein component (ii) is applied as a seed treatment to the crop plant prior to sowing.

10. A method according to claim 6, wherein components (i) and (ii) are applied to the locus as a single, pre-emergence application.

* * * * *